US006902565B2

(12) United States Patent
Berger et al.

(10) Patent No.: US 6,902,565 B2
(45) Date of Patent: Jun. 7, 2005

(54) OCCIPITAL PLATE AND SYSTEM FOR SPINAL STABILIZATION

(75) Inventors: Roger Berger, Bueren (CH); David Gerber, Arborn (CH); Hansjuerg W. Emch, Philadelphia, PA (US); Michael Brace, Lansdale, PA (US)

(73) Assignee: Synthes (U.S.A.), Paoli, PA (US)

( * ) Notice: Subject to any disclaimer, the term of this patent is extended or adjusted under 35 U.S.C. 154(b) by 454 days.

(21) Appl. No.: 09/788,639

(22) Filed: Feb. 21, 2001

(65) Prior Publication Data

US 2002/0120268 A1 Aug. 29, 2002

(51) Int. Cl.$^7$ .......................... A61B 17/56; A61B 17/58; A61F 2/30
(52) U.S. Cl. ............................. 606/61; 606/69; 606/70; 606/71; 606/73
(58) Field of Search ................................ 606/53, 60, 61, 606/65, 69, 70, 71, 72, 73, 104; 623/17.11, 17.16

(56) References Cited

U.S. PATENT DOCUMENTS

| 3,242,922 | A | 3/1966 | Thomas | 128/92 |
| 4,289,123 | A | 9/1981 | Dunn | 128/84 R |
| 4,454,876 | A | 6/1984 | Mears | 128/92 D |

(Continued)

FOREIGN PATENT DOCUMENTS

| DE | 4434574 | 4/1996 |
| DE | 29712285 | 11/1997 |
| EP | 0 308 156 | 3/1989 |
| EP | 0 737 449 A1 | 10/1996 |
| JP | 6-7371 | 11/1994 |
| JP | 9-98984 | 4/1997 |
| WO | WO 94/28813 | 12/1994 |
| WO | WO 95/31147 | 11/1995 |
| WO | WO 98/41160 | 9/1998 |

OTHER PUBLICATIONS

"Occipitocervical Screw Plates," Curtis A. Dickman, in Surgery of the Craniovertebral Junction, Thieme, New York, 1998, pp. 761–808.

"Injuries to the Occipital Cervical Articulation," Paul A. Anderson, in The Cervical Spine, Third Edition, Lippincott–Raven Publishers, Philadelphia, 1998, pp. 387–399.

Current Techniques in Spinal Stabilization, Richard G. Fessler, Ed., McGraw–Hill, New York, 1996, pp. 45–56, 89–92, 101–106.

D. Grob et al., "Posterior Occipitocervical Fusion. A Preliminary Report of a New Technique," Spine, vol. 16, No. 3 Supplement, (1991):S17–S24.

Primary Examiner—Henry Bennett
Assistant Examiner—Kathryn Odland
(74) Attorney, Agent, or Firm—Jones Day

(57) ABSTRACT

An occipitocervical fixation system includes a plate for securing to the occiput and at least one pre-bent rod. The plate includes holes for receiving bone fasteners, and at least one clamping assembly for retaining a portion of a rod. The clamping assembly is selectively pivotable and lockable in place to fix the position of the rod.

69 Claims, 14 Drawing Sheets

U.S. PATENT DOCUMENTS

| | | | |
|---|---|---|---|
| 4,506,662 A | 3/1985 | Anapliotis | 128/92 BC |
| 4,604,995 A | 8/1986 | Stephens et al. | 128/69 |
| 4,773,402 A * | 9/1988 | Asher et al. | 606/61 |
| 4,836,193 A | 6/1989 | Ransford | 128/69 |
| 4,841,959 A | 6/1989 | Ransford | 128/192 YM |
| 4,887,595 A | 12/1989 | Heinig et al. | 606/61 |
| 5,007,909 A | 4/1991 | Rogozinski | 606/61 |
| 5,030,220 A | 7/1991 | Howland | 606/61 |
| 5,092,893 A | 3/1992 | Smith | 623/17 |
| 5,113,685 A | 5/1992 | Asher et al. | 72/458 |
| 5,127,912 A | 7/1992 | Ray et al. | 606/61 |
| 5,147,360 A | 9/1992 | Dubousset | 606/61 |
| 5,300,073 A | 4/1994 | Ray et al. | 606/61 |
| 5,306,275 A | 4/1994 | Bryan | 606/61 |
| 5,360,429 A | 11/1994 | Jeanson et al. | 606/61 |
| 5,366,455 A | 11/1994 | Dove et al. | 606/61 |
| 5,372,598 A | 12/1994 | Luhr et al. | 606/69 |
| 5,415,661 A | 5/1995 | Holmes | 606/69 |
| 5,437,672 A | 8/1995 | Alleyne | 606/61 |
| 5,476,463 A | 12/1995 | Boachie-Adjei et al. | 606/61 |
| 5,507,745 A | 4/1996 | Logroscino et al. | 606/61 |
| 5,527,312 A | 6/1996 | Ray | 606/61 |
| 5,542,946 A | 8/1996 | Logroscino et al. | 606/61 |
| 5,545,164 A | 8/1996 | Howland | 606/61 |
| 5,545,165 A | 8/1996 | Biedermann et al. | 606/61 |
| 5,558,674 A | 9/1996 | Heggeness et al. | 606/61 |
| 5,582,612 A | 12/1996 | Lin | 606/61 |
| 5,593,407 A | 1/1997 | Reis | 606/61 |
| 5,603,713 A | 2/1997 | Aust et al. | 606/61 |
| 5,620,443 A | 4/1997 | Gertzbein et al. | 606/61 |
| 5,624,442 A | 4/1997 | Mellinger et al. | 606/61 |
| 5,630,816 A | 5/1997 | Kambin | 606/61 |
| 5,653,708 A * | 8/1997 | Howland | 606/61 |
| 5,693,053 A | 12/1997 | Estes | 606/61 |
| 5,702,395 A | 12/1997 | Hopf | 606/61 |
| 5,702,452 A | 12/1997 | Argenson et al. | 623/17 |
| 5,704,936 A * | 1/1998 | Mazel | 606/61 |
| 5,709,686 A | 1/1998 | Talos et al. | 606/69 |
| 5,810,815 A | 9/1998 | Morales | 606/61 |
| 5,885,284 A | 3/1999 | Errico et al. | 606/61 |
| 5,891,145 A * | 4/1999 | Morrison et al. | 606/61 |
| 5,899,903 A * | 5/1999 | Cotrel | 606/61 |
| 5,928,233 A | 7/1999 | Apfelbaum et al. | 606/61 |
| 5,947,965 A | 9/1999 | Bryan | 606/61 |
| 5,947,966 A | 9/1999 | Drewry et al. | 606/61 |
| 5,954,722 A * | 9/1999 | Bono | 606/61 |
| 5,976,135 A | 11/1999 | Sherman et al. | 606/61 |
| 5,980,523 A | 11/1999 | Jackson | 606/61 |
| 5,989,251 A | 11/1999 | Nichols | 606/61 |
| 5,993,449 A | 11/1999 | Schlapfer et al. | 606/60 |
| 6,030,389 A | 2/2000 | Wagner et al. | 606/71 |
| 6,106,527 A | 8/2000 | Wu et al. | 606/61 |
| 6,110,173 A | 8/2000 | Thomas, Jr. | 606/61 |
| 6,113,600 A | 9/2000 | Drummond et al. | 606/61 |
| 6,136,003 A | 10/2000 | Hoeck et al. | 606/61 |
| 6,146,382 A * | 11/2000 | Hurlbert | 606/61 |
| 6,171,311 B1 | 1/2001 | Richelsoph | 606/61 |
| 6,179,838 B1 | 1/2001 | Fiz | 606/61 |
| 6,187,005 B1 | 2/2001 | Brace et al. | 606/61 |
| 6,235,033 B1 * | 5/2001 | Brace et al. | 606/69 |
| 6,485,491 B1 * | 11/2002 | Farris et al. | 606/61 |
| 6,524,315 B1 * | 2/2003 | Selvitelli et al. | 606/70 |
| 6,613,050 B1 * | 9/2003 | Wagner et al. | 606/61 |

* cited by examiner

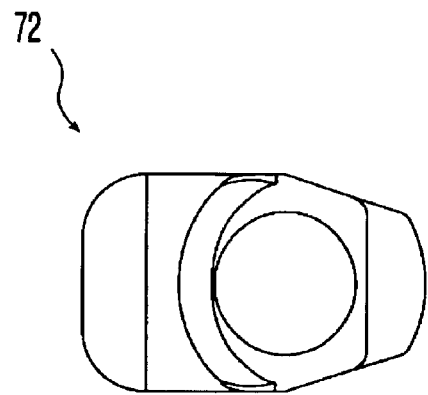
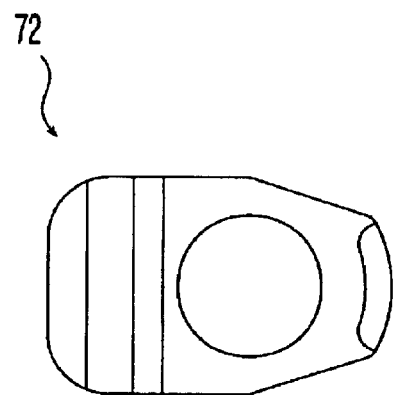
*Fig. 11*  *Fig. 12*
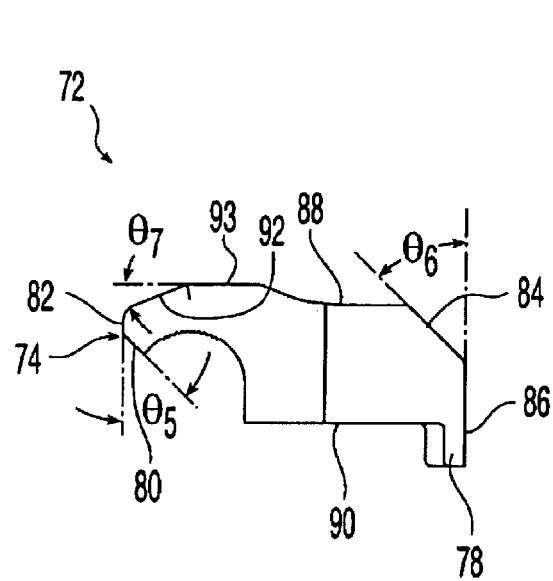
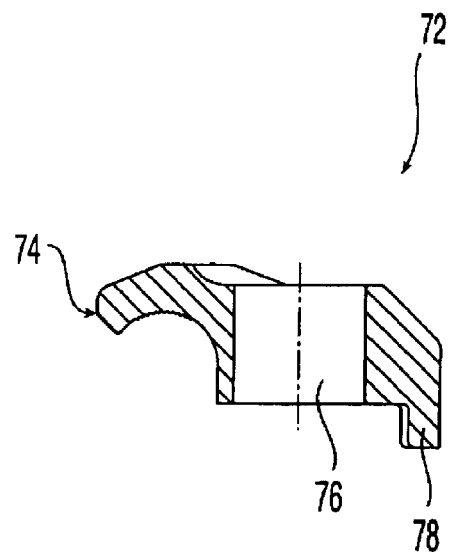
*Fig. 13*  *Fig. 14*

OCCIPITAL PLATE AND SYSTEM FOR SPINAL STABILIZATION

FIELD OF THE INVENTION

The present invention is related to a system for stabilizing the spine. More particularly, the present invention is related to an occipitocervical fixation system that is mounted to both the occiput and spine.

BACKGROUND OF THE INVENTION

Occipitocervical fixation has been achieved using a variety of techniques which generally provide stabilization of the base of the skull with respect to the neck. In order to promote fusion, for example, bone struts formed of autogenous ribs or curved iliac crest struts have been fixed to the occiput and spinous processes, cervical laminae, or facets. Wires are used to fix the struts in place until bone fusion occurs. The thickness of the occiput varies, however, and thus the occiput is typically wired in regions of greater thickness such as near the foramen magnum, at the nuchal line, and along the midline crest. Holes are drilled in the occiput to receive the wires that are also fed through holes in the struts. Although bone fusion occurs with this technique, the struts may be weak prior to fusion, and additional orthosis is applied such as with a halo vest or other hard collar until the struts can provide acceptably strong immobilization. Alternatively, metal struts may be used.

Other techniques for occipitocervical fixation involve the use of other metal implants. One metal implant is a stainless steel, U-shaped device known as a Steinman pin. The threaded pin is bent to match the contour of the occipitocervical region, and fixed to the occiput and cervical laminae or facets using wires. The pin is generally symmetrically disposed about the spine, with the sides of the "U" creating a central region in which a bone graft can be disposed and further wired to the pin. When attached to the occiput and spine, the pin assumes an inverted-U configuration. Several holes are formed in the occiput so that the U-bend may be fixed in place.

Additional metal implants include grooved or roughened titanium rods, smooth steel rods in the form of a Hartshill rectangle or Ransford loop, a Cotrel-Dubousset rod screw plate, and titanium frames have been employed.

Despite these developments, there exists a need for an occipital plate and system for spinal stabilization in which the plate and rod components are separated to permit greater flexibility in installation by the surgeon. In particular, because a traditional unitary plate and rod system is bent in two planes in order to properly adjust it with respect to the occiput, such a unitary design presents difficulties in achieving the desired fit. devices Fixation is using wires that extend through holes formed in the occiput.

SUMMARY OF THE INVENTION

The present invention is related to an occipital plate that includes a Y-shaped plate portion having a front side and a back side, a central portion, two leg portions, and a plurality of bone screw holes in the central portion, the holes being configured and dimensioned to receive a bushing. The occipital plate also includes at least one clamping portion disposed on the front side proximate a free end of at least one of the leg portions, and the plate is bendable to conform to the an occiput. In one embodiment, the central portion includes an upper portion, a lower portion, and a grooved portion therebetween, the upper portion having one bone screw hole. The grooved portion is flexible to permit the upper portion to be disposed at an angle with respect to the lower portion. The leg portions and at least a portion of the central portion are disposed in nonparallel planes, and the planes may intersect at an angle of between about 160° and about 175°, and in one embodiment the planes intersect at an angle of about 170°.

The clamping portion may include a pivot member and a clamp plate, the clamp plate being pivotable about the pivot member. The clamp plate may further include a hole, the pivot member being received in the hole. The pivot member also may include a tapered portion with serrations, and the leg portion may further include a tapered hole with serrations, with the serrations of the tapered portion positively engaging the serrations of the tapered hole. The diameter of the tapered hole increases from the back side to the front side, and the clamp plate is secured to the pivot member with a fastener. The leg portion additionally includes a rod-receiving first recess and the clamping plate additionally includes a rod-receiving second recess, with the first and second recesses generally opposing each other and the second recess being serrated. The bone screw holes in the lower portion may be disposed in a rectangular array, and at least one group of bone screw holes in the array may be disposed along a central axis of the plate extending between the leg portions. The bone screw hole in the upper portion may be disposed on the central axis, and at least two bone screw holes may be disposed coaxially. In one embodiment, the bushings permit polyaxial angulation, the plate is bendable along at least two generally parallel axes and/or at least two generally perpendicular axes.

The present invention is also related to an occipitocernical fixation system including an occipital plate having at least one rod clamp portion and a plate portion with at least one hole for receiving a bone screw, the rod clamp portion having a post, a clamp plate with a hole for receiving the post, and a fastener for tightening the clamp to the post. The system also includes at least one bone screw and at least one rod, with the rod being retained between the plate portion and the clamp plate and being pivotable about the post.

Furthermore, the present invention is related to a pre-bent rod for attachment to an occipital plate including a straight section, a bent section, and a serrated clamping section, with the straight section and the serrated clamping section being disposed substantially perpendicular to each other, and the serrated clamping section and the bent section being disposed at an angle of about 45° with respect to each other. In one embodiment, the serrated clamping section is generally cylindrical and includes circumferential serrations about an angular range of between about 90° and 180°.

BRIEF DESCRIPTION OF THE DRAWINGS

Preferred features of the present invention are disclosed in the accompanying drawings, wherein similar reference characters denote similar elements throughout the several views, and wherein:

FIGS. 11–14 show a top view, bottom view, side view, and partial cross-sectional view, respectively, of a clamping plate according to the present invention;

DETAILED DESCRIPTION OF THE PREFERRED EMBODIMENTS

Figure 1:
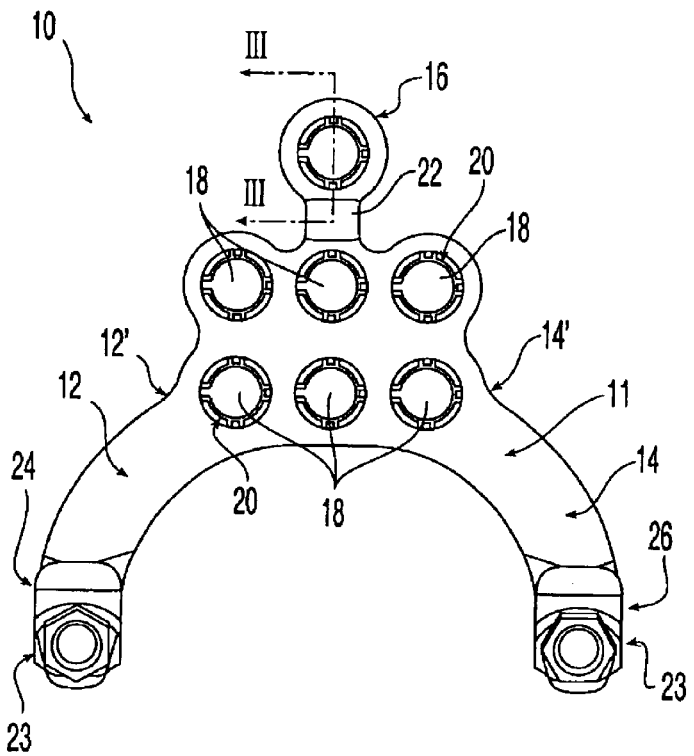
FIG. 1 shows a front view of an occipital plate according to the present invention.
Figure 2:
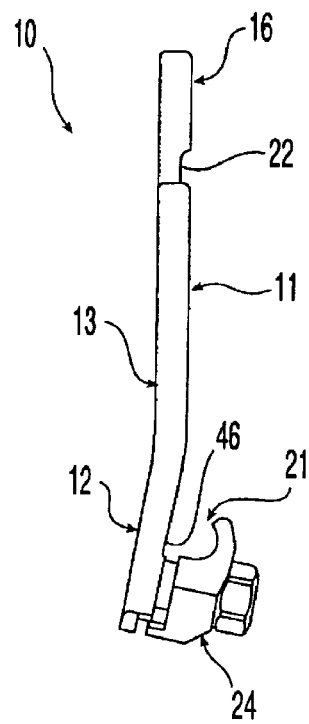
FIG. 2 shows a side view thereof.
Figure 3:
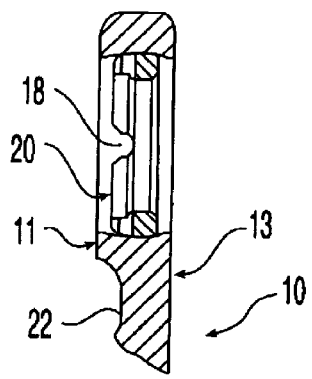
FIG. 3 shows a partial cross-sectional side view of a hole in the occipital plate of FIG. 1 taken along line III—III.

Referring initially to FIGS. 1–3, an occipital plate 10 according to the present invention is shown. In the preferred embodiment, occipital plate 10 is generally Y-shaped with a pair of rod supporting arms 12, 14 and a central extension 16 along with a main portion 17. Holes 18 extending from the front surface 11 to the back surface 13 are provided for receiving bone fasteners (not shown) for fixation of occipital plate 10 to the occiput. Preferably, as shown in FIG. 3, holes 18 are each provided with an expansion head bushing 20 to permit relative angulation of a locking screw or other bone fastener received therein. A grooved region 22 is provided along central extension 16 to facilitate bending of plate 10. In the preferred embodiment, plate 10 may be bent along grooved region 22. In an alternate embodiment, central extension 16 and grooved region 22 may be removed from plate 10. Preferably, grooved region 22 has a thickness that may be accommodated in a rod cutter as used with the rods of the present invention. A clamp assembly 24, 26 is provided proximate the free end of each rod supporting arm 12, 14, respectively, for clamping a portion of a rod against occipital plate 10. Preferably, spinal rods are positionable in clamp assemblies 24, 26, by insertion from the top portion 21 of the assemblies. Alternatively, the rods may be inserted from a side portion 23 of the assemblies. In addition, although the preferred embodiment includes two clamp assemblies, 24, 26, a number other than two may be provided. Rod supporting arms 12, 14 may also be bent, for example near points 12', 14'.

Figure 4:
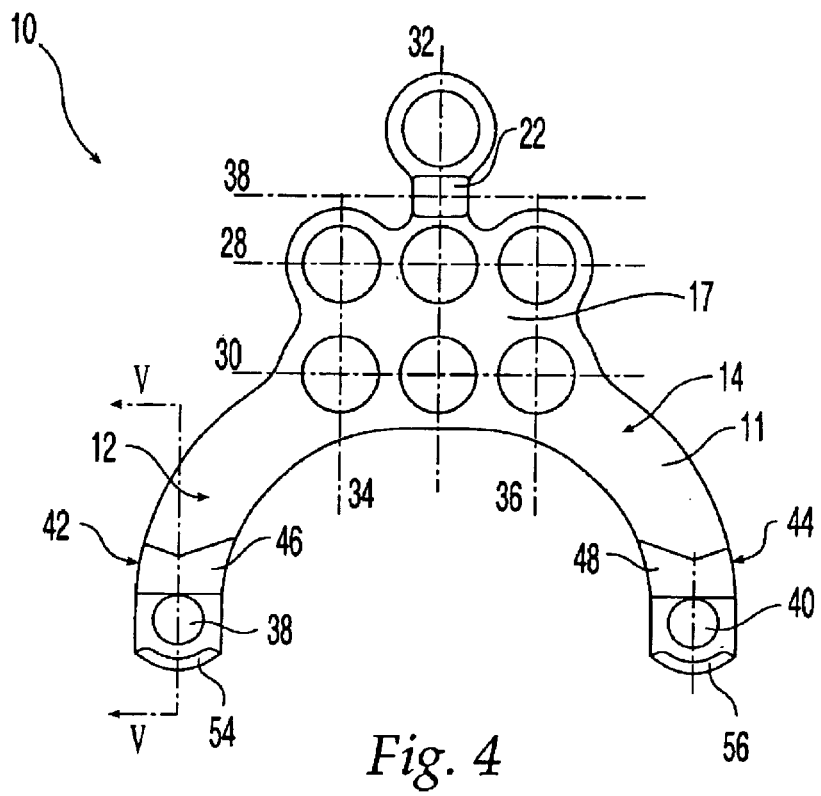
FIG. 4 shows another front view of the occipital plate of FIG. 1 without clamping plates attached thereto.

As shown in FIG. 4, preferably occipital plate 10 includes seven fastener holes 18, with six of the holes 18 aligned in a 2×3 rectangular array. Three holes 18 are aligned along line 28 while three holes 18 are aligned along line 30, with lines 28, 30 being parallel to each other. In addition, while three holes 18 are aligned along central line 32, two holes are aligned long each of lines 34, 26. Lines 32, 34, 36 are parallel to each other and perpendicular to lines 28, 30. In addition, grooved region 22 is aligned along a line 38 which is parallel to lines 28, 30.

Figure 4A:
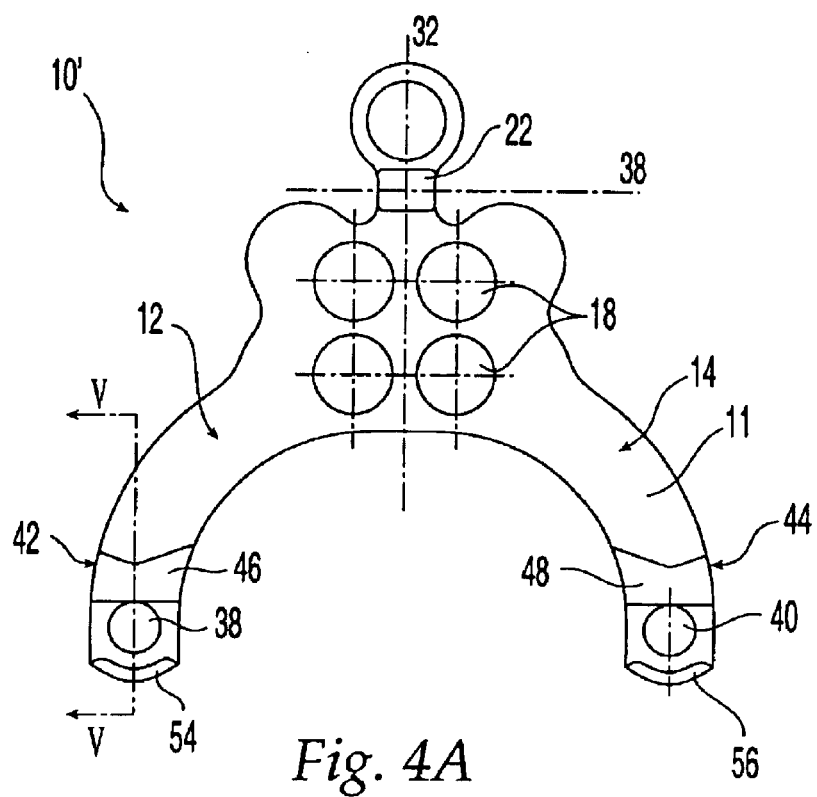
FIGS. 4A–4B show front views of additional embodiments of occipital plates without clamping plates attached thereto.
Figure 4B:
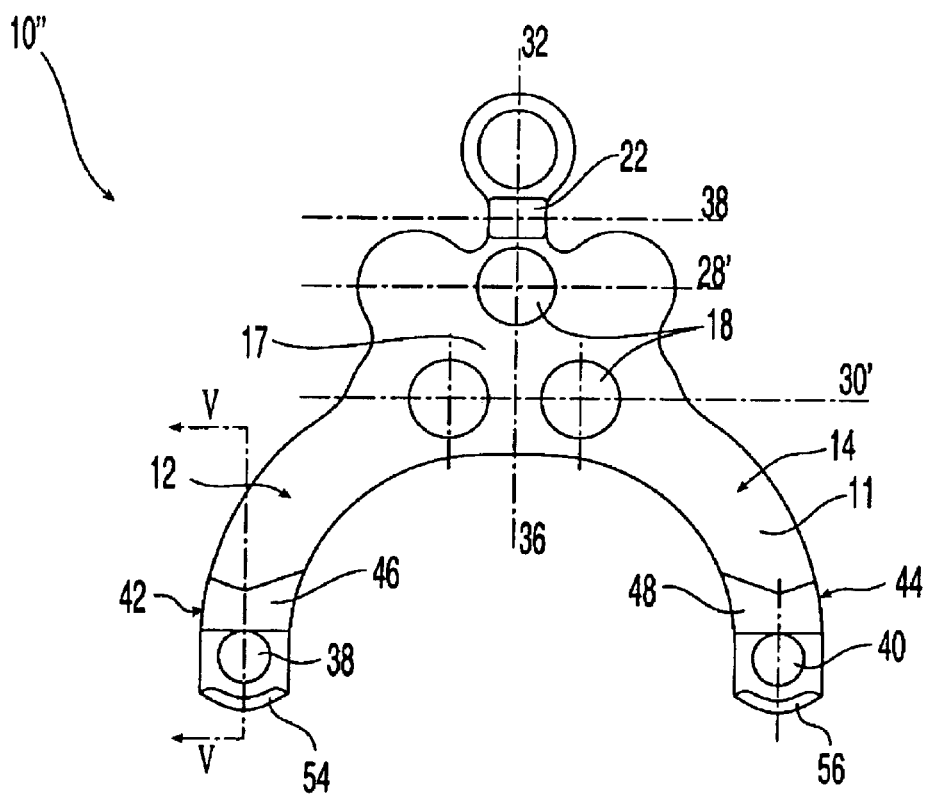

As shown in FIGS. 4A and 4B, additional hole patterns may be used with the occipital plates of the present invention. For example, in FIG. 4A, occipital plate 10' includes four holes 18 that are disposed adjacent line 32, such that the plate may be bent along line 32 without bending along holes 18. In addition, this permits bone screws inserted in holes 18 to be angulated toward the midline 32 of the plate. In FIG. 4B, occipital plate 10" includes a triangular array of holes 18 with one hole along line 28' and another hole along line 30'.

Figure 5:
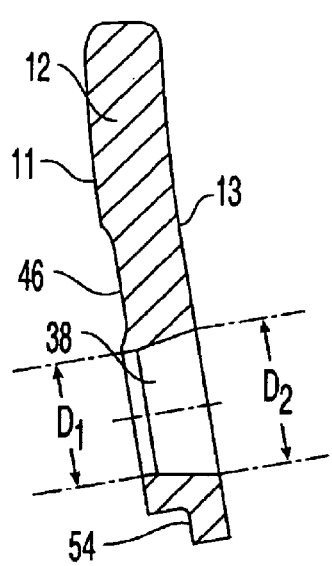
FIG. 5 shows a partial cross-sectional side view of a leg portion of the occipital plate of FIG. 4 taken along line V—V.
Figure 6:
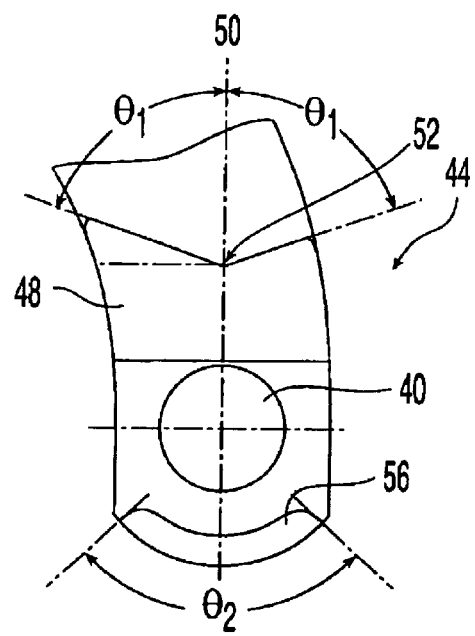
FIG. 6 shows a partial front view of part of a leg portion of the occipital plate of FIG. 4.

Referring particularly to FIGS. 5–6, occipital plate 10 includes holes 38, 40 in lower portions 42, 44 respectively. Holes 38, 40 are configured and dimensioned to receive clamping posts, as will be described. Rod-receiving recesses 46, 48 are generally V-shaped, with each leg of the "V" extending at an angle θ with respect to a line 50 extending through V-notch 52 and the center of hole 40, and further aligned parallel to lines 32, 34, 36. In the preferred embodiment, angle $\theta_1$ is between about 60° and about 80°, and more preferably about 70°. Arcuate stepped-in portions 54, 56 are disposed along the lowermost regions of rod supporting arms 12, 14, and preferably extend through a total angle of about 80° and about 120°, and more preferably about 100°, symmetrically with respect to line 50. As shown in FIG. 5, holes 38, 40 are preferably tapered with a first diameter $D_1$ on front surface 11 being smaller than a second diameter $D_2$ on back surface 13.

Figures 7, 8:
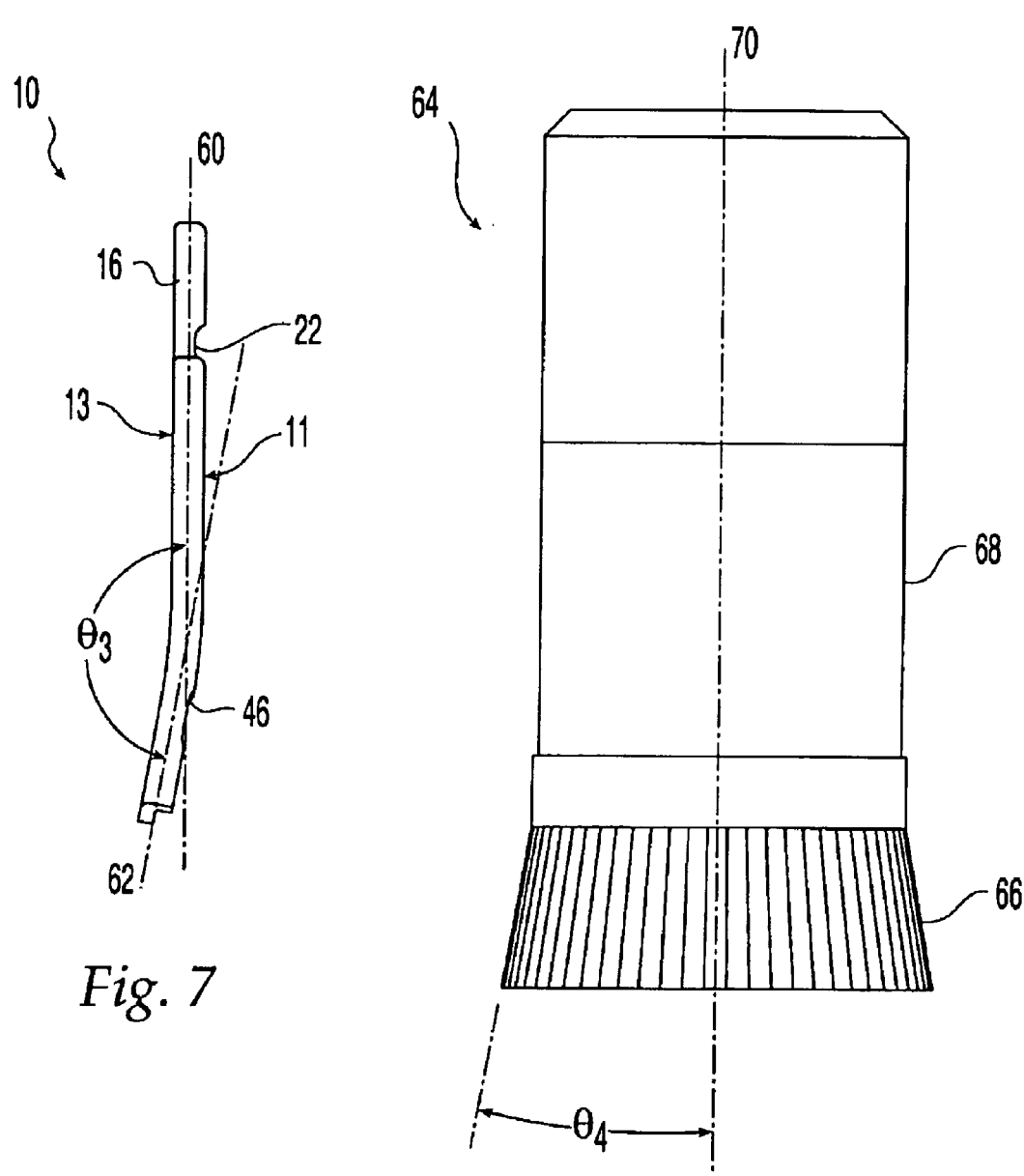
FIG. 7 shows a side view of the occipital plate of FIG. 4.
FIG. 8 shows a post according to the present invention.

With reference to FIG. 7, central extension 16 is disposed along a plane 60, while rod supporting arms 12, 14 are disposed along a plane 62. Planes 60, 62 are not coplanar, and form an angle $\theta_3$ with respect to each other that is preferably between about 160° and about 175°, and more preferably about 170°.

Figure 9:
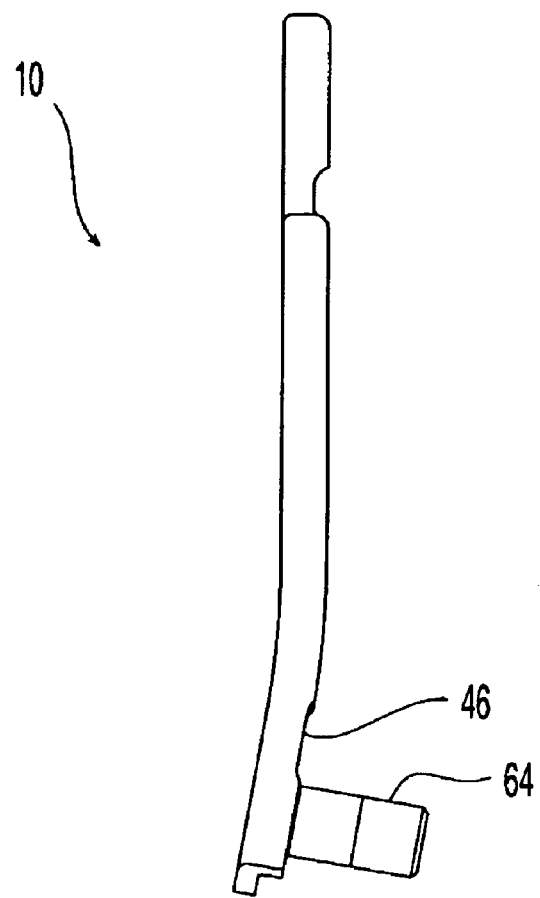
FIGS. 9 and 10 show a side view and a partial cross-sectional side view, respectively, of the occipital plate of FIG. 7 with a post inserted therein.
Figure 10:
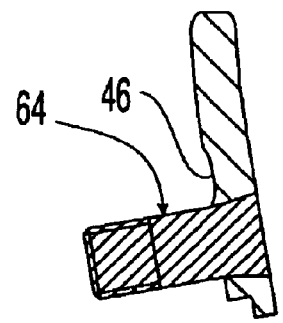
Figure 15:
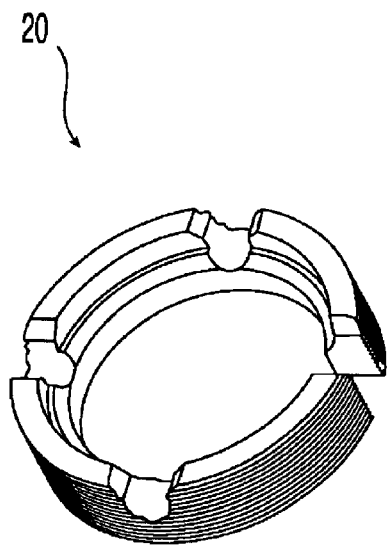
FIGS. 15–18 show a perspective view, top view, partial cross-sectional view through line XVII—XVII, and partial cross-sectional view through line XVIII—XVIII, respectively, of a bushing for use with the present invention.
Figure 16:
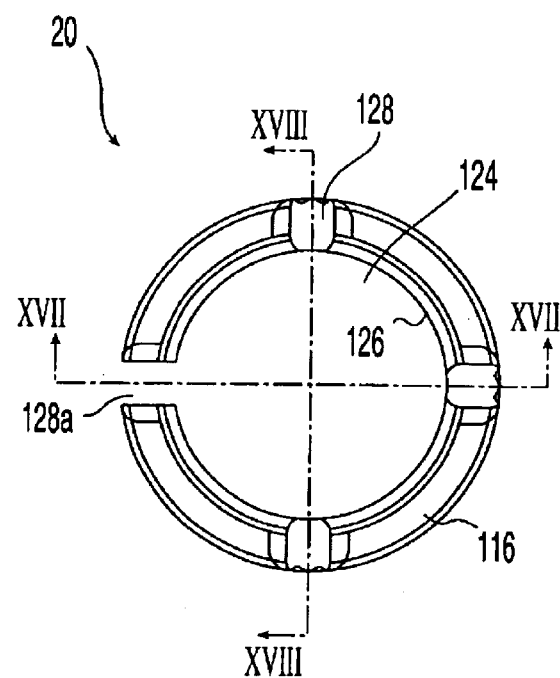
Figure 17:
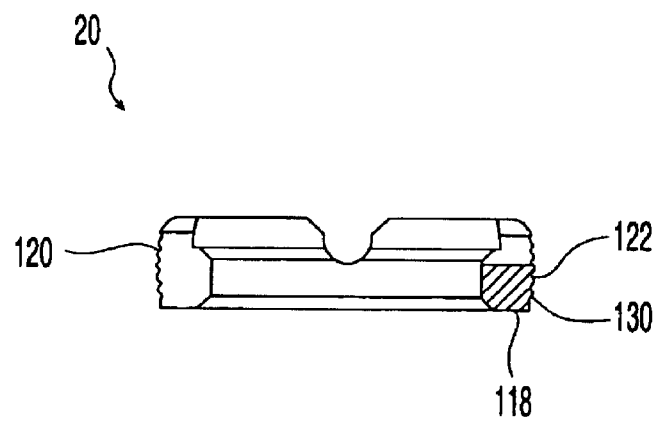
Figure 18:
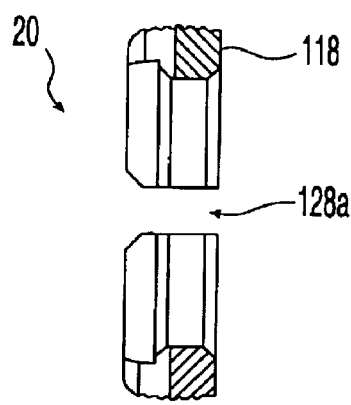

Turning to FIGS. 8–10, a post 64 is shown. One post 64 is placed in each hole 38, 40 such that the tapered head 66 rests in the hole. Preferably, taper head 66 tapers at an angle $\theta_4$ of between about 5° and 15° and more preferably about 10° with respect to the central axis 70 of post 64, and this taper angle is also present in holes 38, 40. A post 64 installed in a hole 38 is shown in FIGS. 9–10. Preferably, head 66 is provided with serrations that interlock with serrations on the inside surface of a hole 38, 40 so that a positive mechanical engagement can be achieved to assist in locking a post 64 in place with respect to the occipital plate 10. Post 64 also includes a body portion 68, which preferably is at least partially threaded for receiving a nut or other like-threaded fastening device.

Referring to FIGS. 11–14, a clamp plate 72 for use as a part of a clamp assembly 24, 26 is shown. Clamp plate 72 includes a hooked serrated portion 74 for engagement with a longitudinal rod, and further includes a central pivoting hole 76 in which a post 64 is received. A leg 78 of each clamp plate 72 is received in an arcuate stepped-in portion 54, 56 of a rod supporting arm 12, 14. Front edge 80 of clamp plate 72 is disposed at an angle $\theta_5$ with respect to top edge 82, and preferably angle $\theta_5$ is about 45°. Back edge 84 is disposed at an angle $\theta_6$ with respect to rear edge 86, and preferably angle $\theta_6$ is about 38°. Outer and inner sides 88, 90, respectively, are substantially parallel with respect to each other. Edge 92 is disposed at an angle $\theta_7$ with respect to edge 93, with angle $\theta_7$ preferably being about 22°.

Turning briefly to FIGS. 15–18, a bushing 20 for use with the present invention is shown. Bushing 20 has an upper surface 116, a lower surface 118, and a sidewall 120. Sidewall 120 has an exterior surface 122 configured and dimensioned for polyaxial rotation within a through hole 18. As a result and as described in more detail below, a fastener inserted through a bore 124, which is defined by an interior surface 126 of bushing 20 and extends through both upper and lower surfaces 116, 118, can be inserted at a wide variety of orientations relative to occipital plate 10. In an exemplary embodiment, bushing 20 has a frustospherical shape. Alternatively, bushing 20 can have a frustoconical shape. With either shape, bore 124 can extend through the central longitudinal axis perpendicular to the parallel upper and lower surfaces 116, 118.

Bushing 20 includes slots 128 located on sidewall 120. Slots 128 allow sidewall 120 to expand outwardly against through hole 18. This outward expansion locks bushing 20 at the selected orientation relative to the axis of through hole 18. In order to enhance the locking effect upon expansion, exterior surface 122 of sidewall 120 and/or the periphery of through holes 18 can be provided with ridges 130. Ridges 130 provide an additional mechanism to resist motion of bushing 20 relative to occipital plate 10 once sidewall 120 has expanded outwardly. Although bushing 20 is shown having four slots, any number of slots, including one, can be used as long as the chosen number of slots provides for outward expansion of sidewall 120. Slot 128a extends from upper surface 116 through lower surface 118 while the rest of slots 128 do not extend through to lower surface 118. Slots 128 all extend from upper surface 116 of bushing 20.

Figures 19, 20, 21:
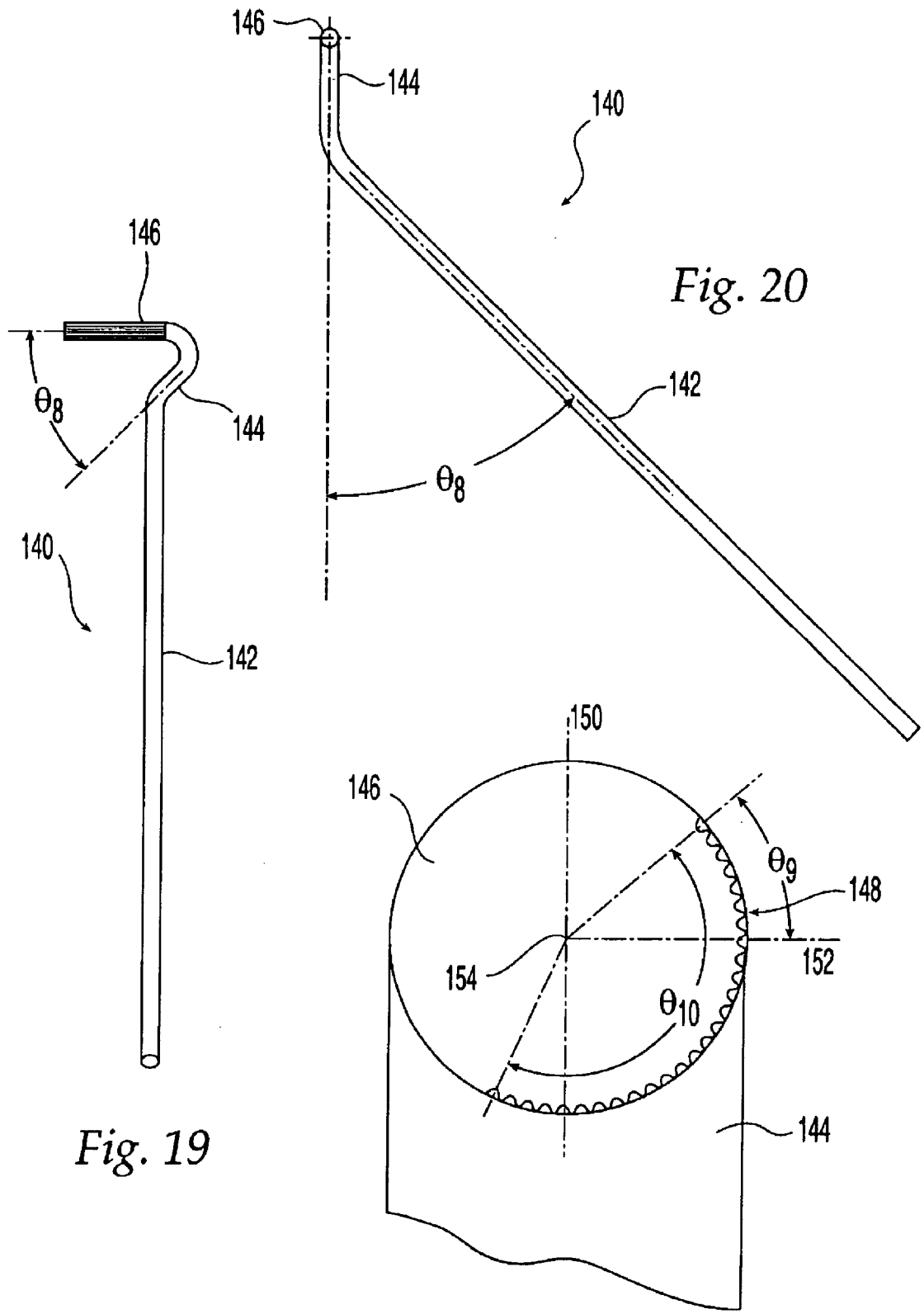
FIGS. 19 and 19A show a front view of a first embodiment of a right prebent rod and a left pre-bent rod, respectively, according to the present invention.
FIG. 20 shows a side view of the pre-bent rod of FIG. 19.
FIG. 21 shows a side view of the serrated clamping section of FIG. 20.

In the preferred embodiment, pre-bent rods suitable for use with the present invention are shown in FIGS. 19–21. Each rod 140 includes a straight section 142 for running generally parallel to the spine, a bent section 144, and a serrated clamping section 146. Sections 142, 146 are substantially perpendicular to each other, while sections 144, 146 are disposed at an angle $\theta_8$ with respect to each other. Preferably, angle $\theta_8$ is between about 40° and about 50°, and more preferably approximately 45°. As shown in FIG. 21, serrated clamping section 146 includes serrations 148 about a portion of its circumference. When bent section 144 is aligned with vertical line 150, and section 146 is centered at the intersection of perpendicular lines 150, 152, it can be seen from FIG. 21 that serrations 148 only extend through an angle $\theta_9$ from line 152. Preferably, angle $\theta_9$ is between about 30° and about 50°, and more preferably about 41°. Moreover, serrations 148 are present along the circumference of section 146 of rod 148 through a total angular range $\theta_{10}$ as measured from center point 154. Preferably, $\theta_{10}$ is between about 90° and 180°, and more preferably $\theta_{10}$ is about 156°.

Figure 19A:
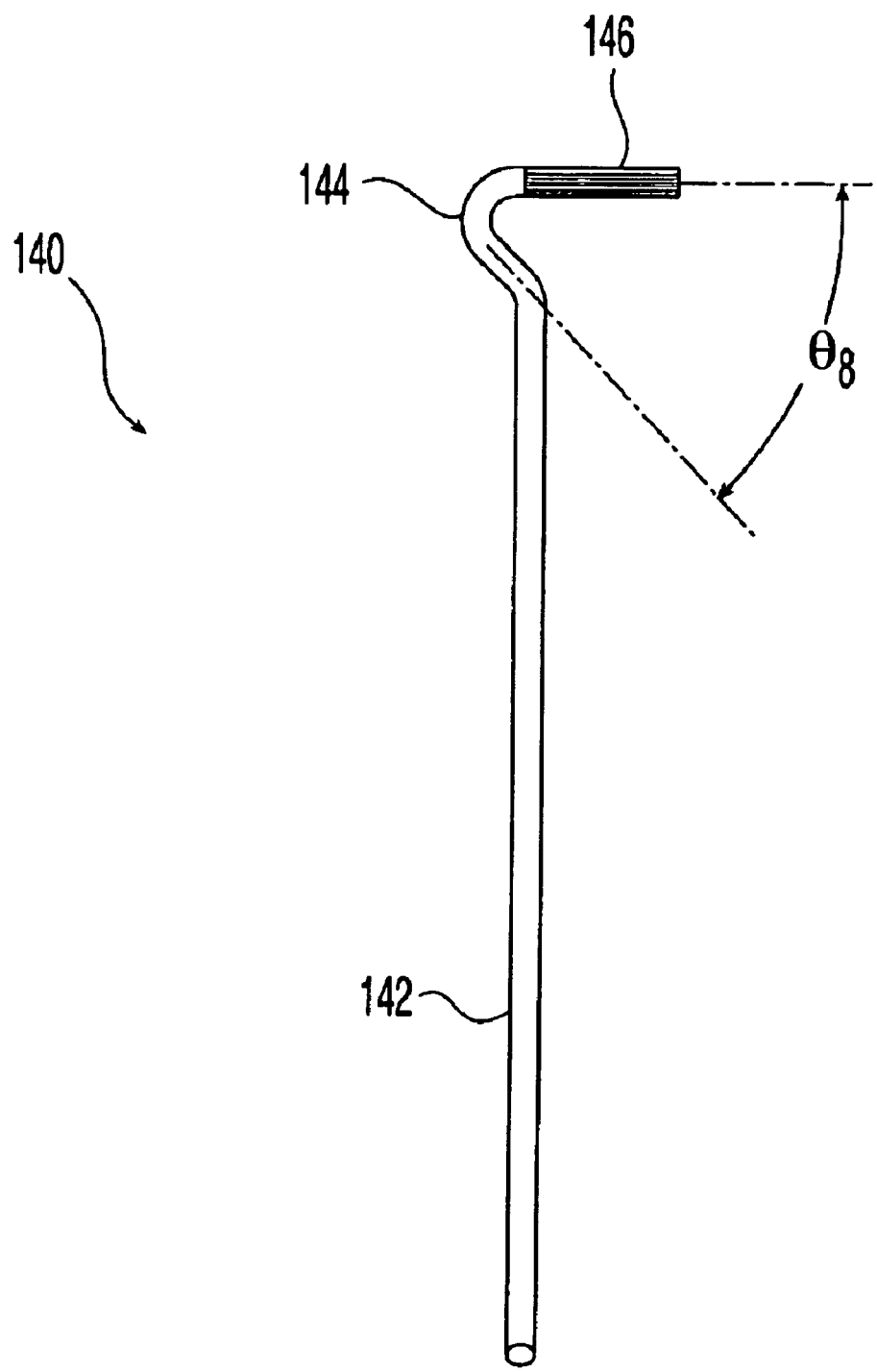

The pair of rods used with occipital plate 10 are typically mirror images of each other. For example, a rod 140 would be used with right clamp assembly 26 while a mirror image of rod 140, as shown in FIG. 19A, would be used with left clamp assembly 24.

Figure 22:
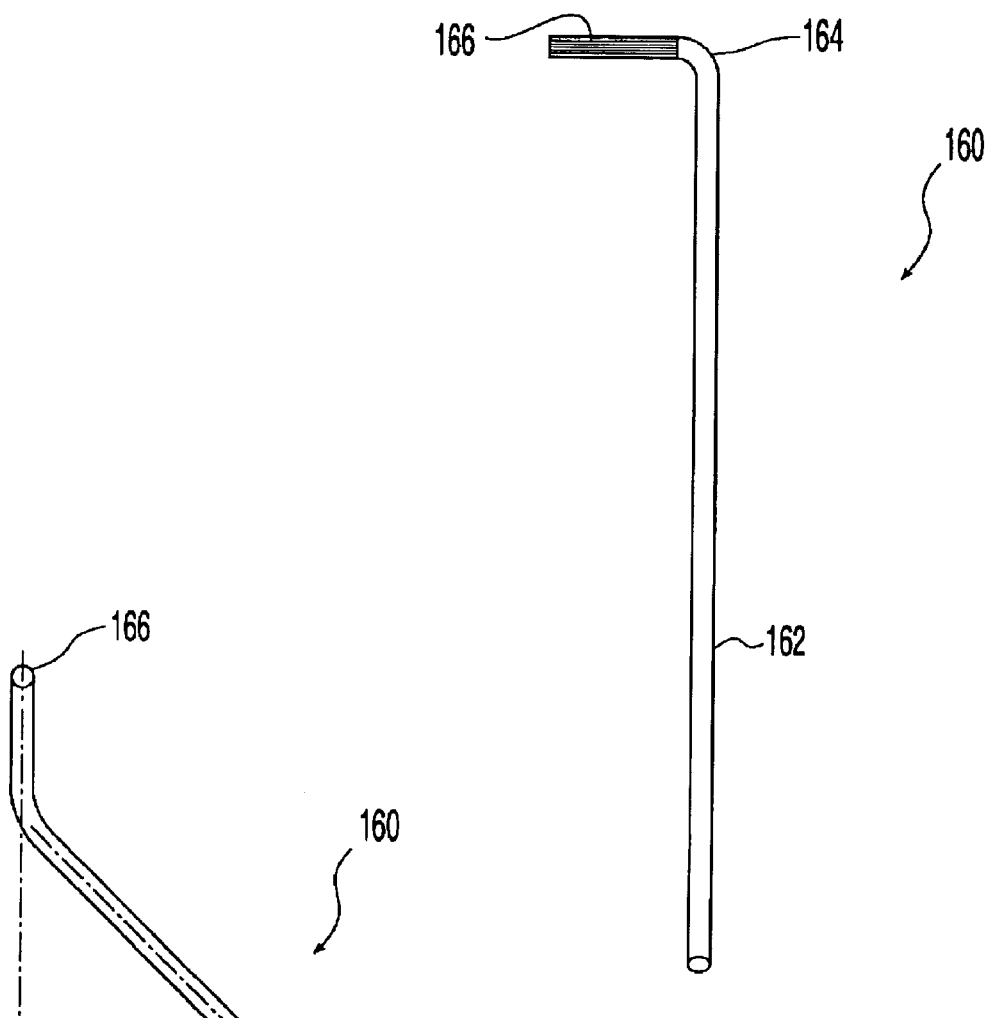
FIGS. 22–23 show a front view and a side view of a second embodiment of a pre-bent rod according to the present invention.
Figure 23:
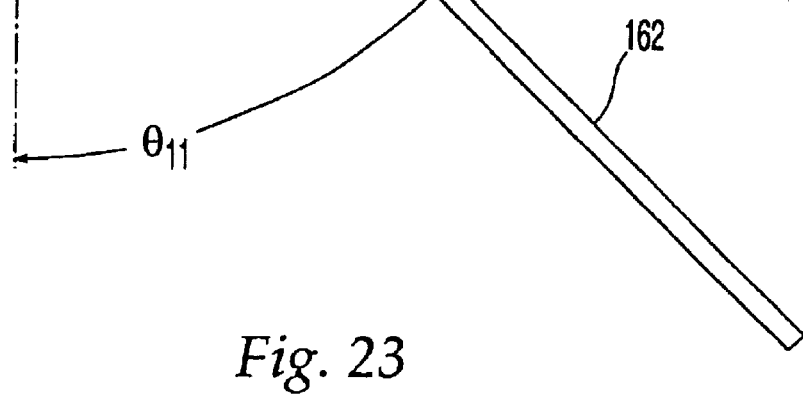

In an alternate embodiment shown in FIGS. 22–23, pre-bent rod 160 includes a straight section 162 for running generally parallel to the spine, a transition section 164, and a serrated clamping section 166. Sections 162, 166 are substantially perpendicular to each other, while sections 164, 166 are disposed at an angle $\theta_{11}$ with respect to each other. Preferably, angle $\theta_{11}$ is between about 40° and about 50°, and more preferably approximately 45°.

Figure 24:
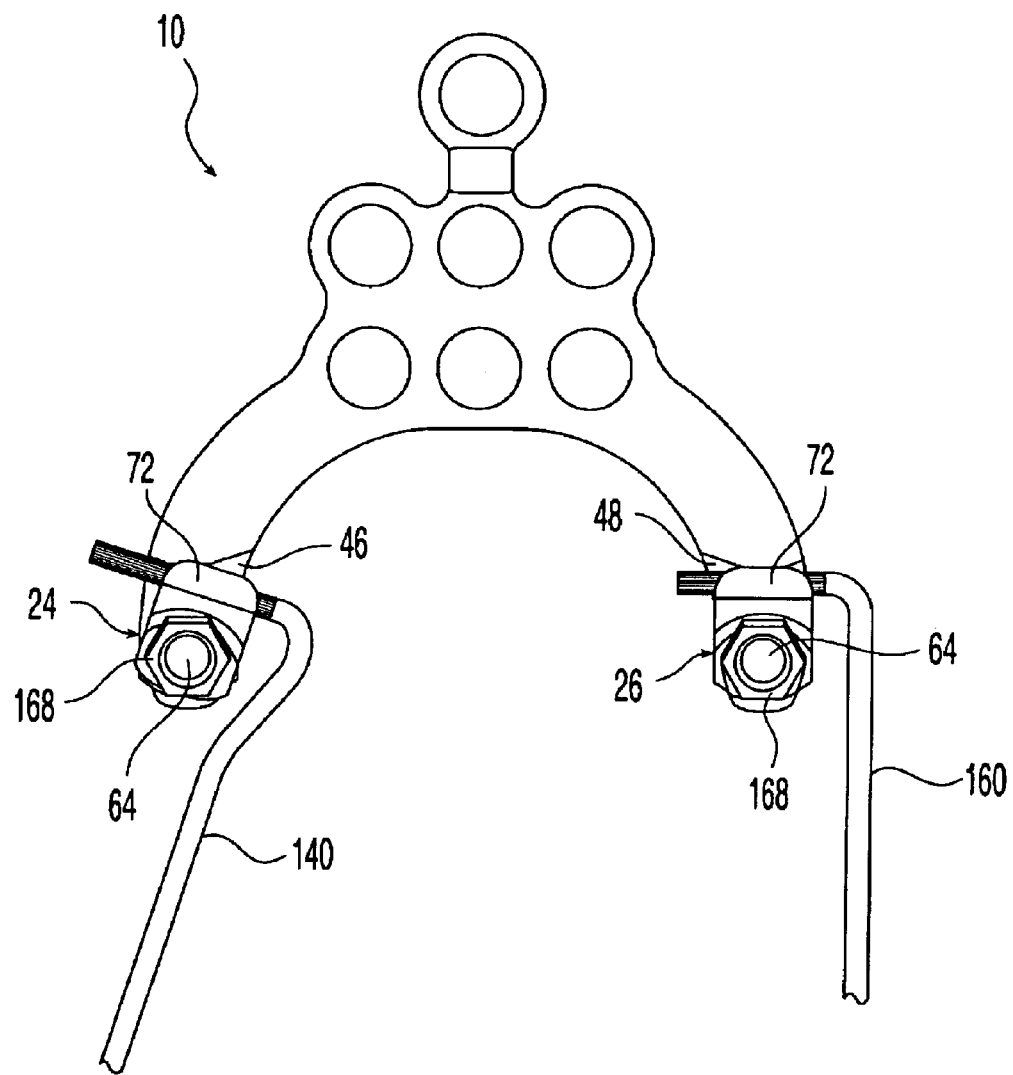
FIG. 24 shows an occipital plate with first and second embodiments of the pre-bent rods of FIGS. 19–23.
Figure 25:
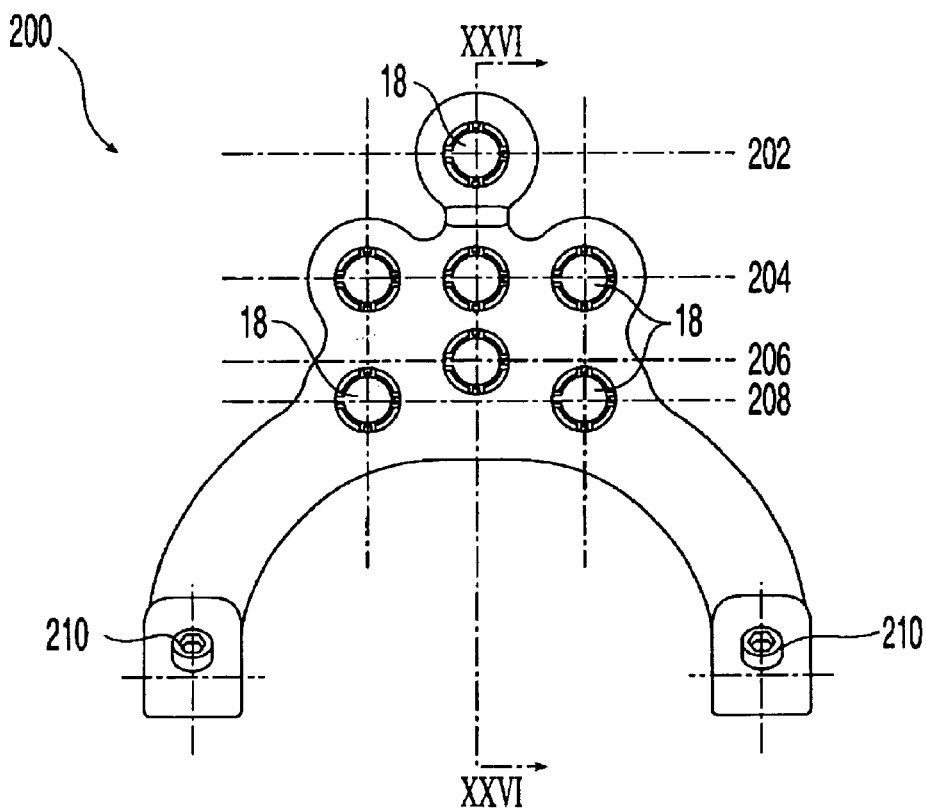
FIGS. 25–26 show a front view and a partial cross-sectional side view of another embodiment of an occipital plate according to the present invention.
Figure 26:
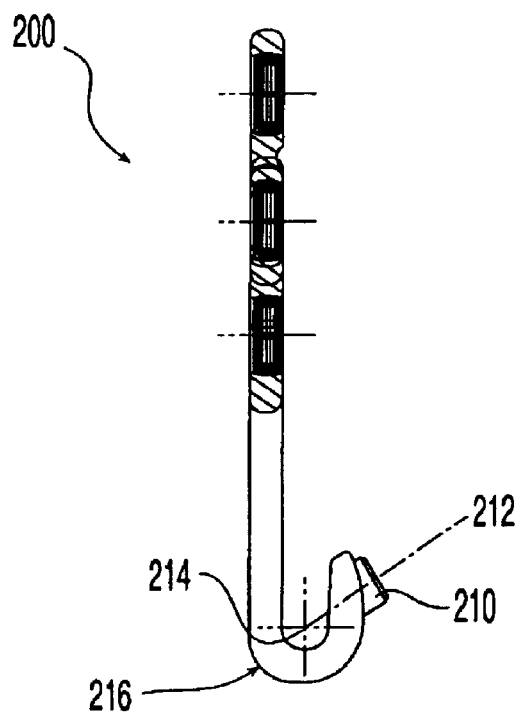

Pre-bent rods 140, 160 are shown retained in clamp assemblies 24, 26, respectively, in FIG. 24. Although the pair of rods used with occipital plate 10 are typically mirror images of each other, for illustrative purposes only, one of each rod 140, 160 is shown. As seen particularly with regard to clamp assembly 24, clamp plate 72 rotates about post 64, and may be fixed in place using a nut 168. Rod receiving recesses 46, 48 are used to further lock a rod 140, 160 in place.

Figure 27:
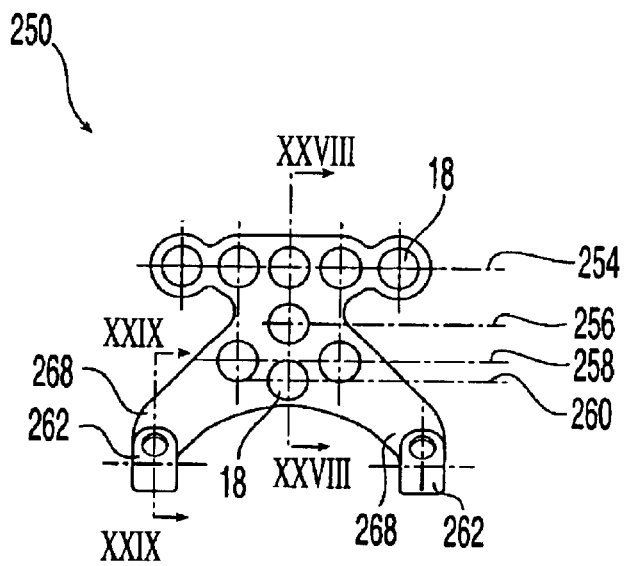
FIGS. 27–29 show a front view side view, and partial cross-sectional side view of yet another embodiment of an occipital plate according to the present invention.
Figure 28:
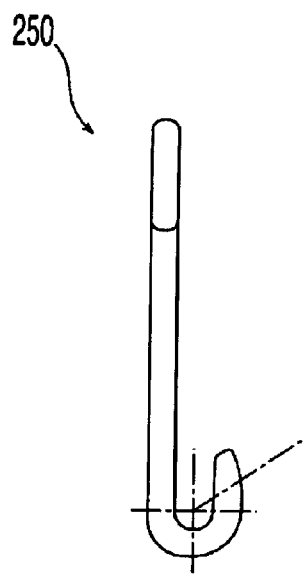
Figure 29:
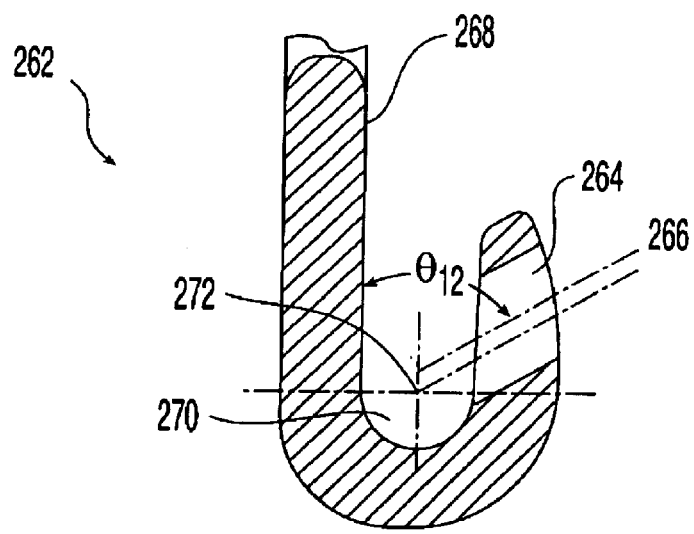

Alternate embodiments of occipital plates are shown in FIGS. 25–31. First referring to FIGS. 25–26, similar to occipital plate 10, occipital plate 200 includes seven holes 18 for receiving bone fasteners. However, in this embodiment, holes 18 are disposed about four parallel lines 202, 204, 206, 208 instead of three. In addition, as shown particularly in FIG. 26, pre-bent rods are clamped to occipital plate 200 using set screws 210 extending through a U-shaped or C-shaped section 216, and which are disposed about an axis 212 that may be aligned with or slightly offset from the center of a rod held in region 214. Another embodiment is shown in FIGS. 27–29, in which an occipital plate 250 is provided with nine holes 18 disposed about four parallel lines 254, 256, 258, 260. As with occipital plate 200, sections 262 are provided for clamping spinal fixation rods to occipital plate 250. A threaded set screw (not shown) is threadably received in like-threaded hole 264, which is preferably aligned along an axis 266 disposed at an angle $\theta_{12}$ with respect to plate wall 268. Preferably, angle $\theta_{12}$ is between about 50° and about 70°, and more preferably about 60°. Again, threaded hole 264 aligns a set screw to be offset from the center of a rod seated in region 270 and centered about point 272.

Figure 30:
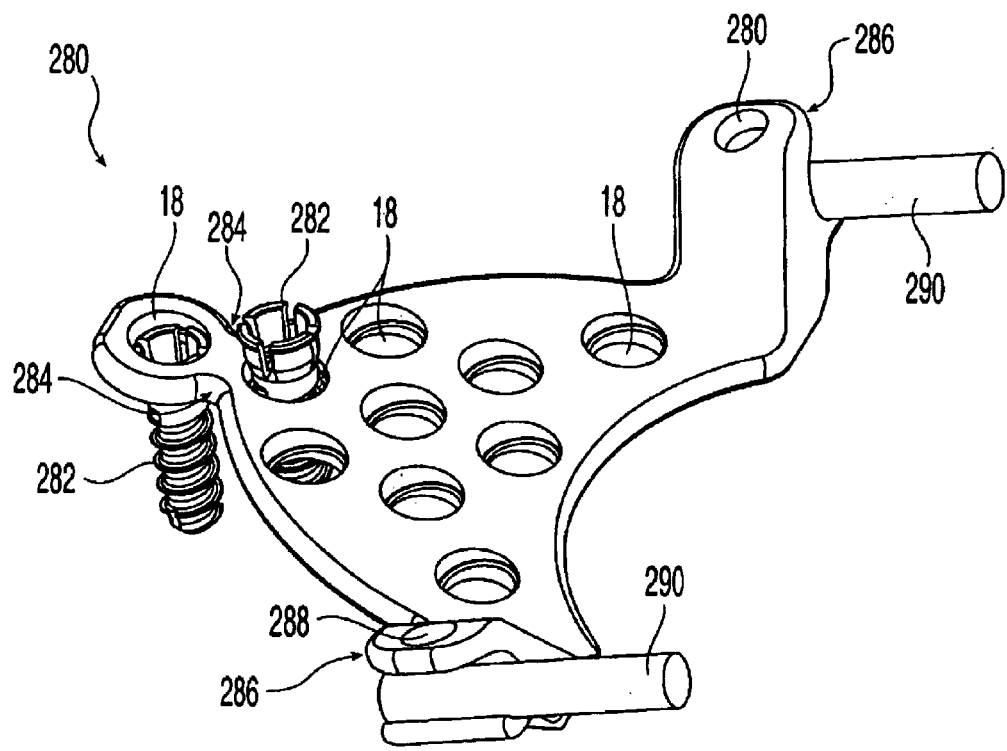
FIGS. 30–31 show perspective view of additional embodiments of occipital plates according to the present invention.
Figure 31:
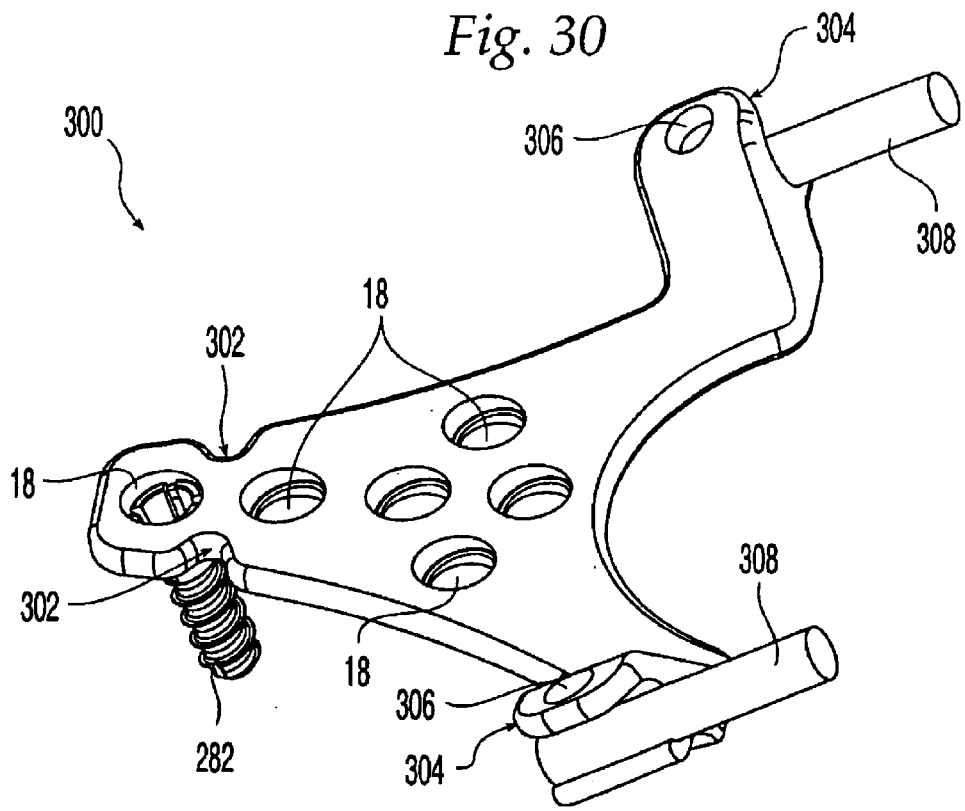

Additional embodiments of occipital plates are shown in FIGS. 30–31. Notably, expansion head screws 282 are shown installed or partially installed in plate holes 18. Occipital plates 280, 300 include notched regions 284, 302, respectively, to facilitate bending. Also, side clamping assemblies 286, 304 receive rods 290, 308 that are fixed with a set screw extending in holes 288, 306, respectively. Preferably, side clamping assemblies 286, 304 are angulated such that rods 290, 308 are disposed at an angle of between about 20° and about 30°, and more preferably about 25° with respect to the plane of the plate prior to bending.

In some preferred embodiments of the present invention, cylindrical rods with a diameter of 3.5 mm are used as the spinal rods or pre-bent rods. In alternate embodiments, straight rods may be used and oriented accordingly by a surgeon using a rod bender.

In the occipital plate designs disclosed herein, screw holes have been positioned along the midline of the plate for use at the midline of the occiput, since the bone thickness there is greater than on the sides. In some embodiments, the screw holes may be angled about 12° to facilitate access to the screws with a screwdriver, and to enhance pull-out strength of the screws due to the wedge effect. Although expansion head screws are preferred, other non-locking screws may be used. Arc shaped cuts between the clamping assemblies or arrangements of each plate allow the placement of a bone graft. In the preferred embodiment, occipital plate 10 is formed of titanium. Preferably, the shape of the occipital plate facilitates polyaxial bending thereof.

The number of holes provided in an occipital plate of the present invention for receiving bone screws may be varied, as may the pattern of the holes and the relative alignment. Other screw hole shapes such as an oval shape, and other hole sizes may be used, as well as alternative means for locking screws. Bushings may not be included in some embodiments. Alternative fasteners for attaching an occipital plate to bone include staples and wires.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, the C-shaped clamping sections of some embodiments of the occipital plate may instead include full-circle regions for receiving rods. In another embodiment, a sleeve for receiving the rods may extend across some or the entire the length of the occipital plate. In yet another embodiment, two smaller occipital plates are provided for securement to the occiput, with each plate having a single clamp assembly and receiving one rod. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An occipital plate comprising:
   a Y-shaped plate portion having a front side and a back side, a central portion, at least two leg portions, a plurality of bone screw holes in the central portion, and at least one bushing; wherein the holes are configured and dimensioned to receive the bushing; and
   at least one clamping portion disposed on the front side proximate a free end of one of the at least two leg portions; wherein the clamping portion comprises a pivot member and a clamp plate, the clamp plate being pivotable about the pivot member and includes an extension sized and configured to engage an arcuate stepped-in portion formed on the leg portion of the plate to limit the amount of pivot between the clamp plate and the plate.

2. The occipital plate of claim 1, wherein the central portion includes an upper portion, a lower portion, and a grooved portion therebetween, the upper portion having one bone screw hole.

3. The occipital plate of claim 2, wherein the grooved portion is flexible to permit the upper portion to be disposed at an angle with respect to the lower portion.

4. The occipital plate of claim 2, wherein the leg portions and at least a portion of the central portion are disposed in nonparallel planes.

5. The occipital plate of claim 4, wherein the planes intersect at an angle of between about 160° and about 175°.

6. The occipital plate of claim 5, wherein the planes intersect at an angle of about 170°.

7. The occipital plate of claim 1, wherein the clamp plate further comprises a hole, the pivot member being received in the hole.

8. The occipital plate of claim 7, wherein the pivot member further comprises a tapered portion with serrations, and the leg portion further comprises a tapered hole with serrations, wherein the serrations of the tapered portion positively engage the serrations of the tapered hole.

9. The occipital plate of claim 8, wherein the diameter of the tapered hole decreases from the back side to the front side.

10. The occipital plate of claim 9, wherein the clamp plate is secured to the pivot member a fastener.

11. The occipital plate of claim 1, wherein the leg portion additionally comprises a rod-receiving first recess and the clamping plate additionally comprises a rod-receiving second recess, the first and second recesses generally opposing each other.

12. The occipital plate of claim 11, wherein the second recess is serrated.

13. The occipital plate of claim 2, wherein the bone screw holes in the lower portion are disposed in a rectangular array.

14. The occipital plate of claim 13, wherein at least one group of bone screw holes in the array is disposed along a central axis of the plate extending between the leg portions.

15. The occipital plate of claim 14, wherein the bone screw hole in the upper portion is disposed on the central axis.

16. The occipital plate of claim 2, wherein at least two bone screw holes are disposed coaxially.

17. The occipital plate of claim 1, wherein the bushings permit polyaxial angulation.

18. The occipital plate of claim 1, wherein the plate is bendable along at two generally parallel axes.

19. The occipital plate of claim 1, wherein the plate is bendable along at least two generally perpendicular axes.

20. The occipital plate of claim 17, wherein the exterior surface of the bushing has a frustospherical shape.

21. The occipital plate of claim 17, wherein the bushing further includes at least one slot located on a sidewall thereof.

22. The occipital plate of claim 21, wherein the sidewall further includes a ridge.

23. The occipital plate of claim 11, wherein the rod-receiving first recess has a V-shaped recess.

24. An occipitocervical fixation system comprising:
   an occipital plate comprising a plate portion with at least one hole for receiving a bone screw, and at least two rod clamp portions extending therefrom, at least one of the rod clamp portions having a post, a pivotable clamp plate with a hole for receiving the post, and a fastener for tightening the clamp plate to the post; and
   at least one rod, wherein the rod is retained between the clamp plate and one of the rod clamp portions, the clamp plate being pivotable about the post,
   wherein the plate further includes an arcuate stepped-in portion adjacent the post and the clamp plate further includes an extension sized and configured to engage the arcuate stepped-in portion.

25. The occipitocervical fixation system of claim 24, wherein the arcuate stepped in-portion extends through an angle of about 80 degrees to about 120 degrees.

26. The occipitocervical fixation system of claim 24, wherein the plate further includes a post hole sized and configured to receive the post.

27. The occipitocervical fixation system of claim 26, wherein the post further comprises a tapered portion with serrations, and the post hole further comprises a tapered hole with serrations, wherein the serrations of the tapered portion positively engage the serrations of the tapered hole.

28. The occipitocervical fixation system of claim 27, wherein the diameter of the tapered hole decreases from the back side to the front side.

29. The occipitocervical fixation system of claim 26, wherein the plate further comprises a rod-receiving first recess and the clamp plate further comprises a rod-receiving second recess, the first and second recesses generally opposing each other.

30. The occipitocervical fixation system of claim 29, wherein the second recess is serrated.

31. The occipitocervical fixation system of claim 29, wherein the rod-receiving first recess has a V-shaped recess.

32. The occipitocervical fixation system of claim 24, wherein the rod is positionable in one of the at least two clamp positions by insertion from a top portion of the assembly.

33. The occipitocervical fixation system of claim 24, wherein the plate portion has an upper portion, a lower portion, and a grooved portion therebetween, the upper portion having one bone screw hole.

34. The occipitocervical fixation system of claim 33, wherein the grooved portion is flexible to permit the upper portion to be disposed at an angle with respect to the lower portion.

35. The occipitocervical fixation system of claim 33, wherein the bone screw holes in the lower portion are disposed in a rectangular array.

36. The occipitocervical fixation system of claim 35, wherein at least one group of bone screw holes in the array is disposed along a central axis of the plate extending between the leg portions.

37. The occipitocervical fixation system of claim 36, wherein the bone screw hole in the upper portion is disposed on the central axis.

38. The occipitocervical fixation system of claim 33, wherein at least two bone screw holes are disposed coaxially.

39. The occipitocervical fixation system of claim 24, wherein the rod clamp portion and the plate portion are disposed in nonparallel planes.

40. The occipitocervical fixation system of claim 39, wherein the planes intersect at an angle of between about 160° and about 175°.

41. The occipitocervical fixation system of claim 39, wherein the planes intersect at an angle of about 170°.

42. The occipitocervical fixation system of claim 24, wherein the plate further includes a bushing; the at least one bone screw hole being sized and configured to receive the bushing to permit polyaxial angulation.

43. The occipitocervical fixation system of claim 42, wherein the exterior surface of the bushing has a frustospherical shape.

44. The occipitocervical fixation system of claim 42, wherein the bushing further includes at least one slot located on a sidewall thereof.

45. The occipitocervical fixation system of claim 44, wherein the sidewall further includes a ridge.

46. The occipitocervical fixation system of claim 24, wherein the plate is bendable along at least two generally parallel axes.

47. The occipitocervical fixation system of claim 24, wherein the plate is bendable along at least two generally perpendicular axes.

48. An occipital plate comprising:
a front side and a back side, a central portion, and at least two leg portions extending from the central portion, at least one of the leg portions having a V-shaped rod-receiving first recess and an arcuate stepped-in portion;
at least one bone screw hole in the central portion;
at least one pivotable clamping portion disposed on the front side of one of the at least two leg portions;
wherein the at least one of the leg portions includes a post hole and the at least one clamping portion includes a pivot member and a clamp plate; the pivot member being sized and configured to mate with the clamp plate and the post hole and the clamp plate includes a rod-receiving second recess sized and configured to align with the V-shaped first recess and an extension sized and configured to engage the arcuate stepped-in portion.

49. The occipital plate of claim 48, wherein the arcuate stepped in-portion extends through an angle of about 80 degrees to about 120 degrees.

50. The occipital plate of claim 48, wherein the pivot member further comprises a tapered portion with serrations, and the post hole further comprises a tapered hole with serrations, wherein the serrations of the tapered portion positively engage the serrations of the tapered hole.

51. The occipital plate of claim 50, wherein the diameter of the tapered hole decreases from the back side to the front side.

52. The occipital plate of claim 48, wherein the clamp plate is secured to the pivot member with a fastener.

53. The occipital plate of claim 48, wherein the second recess is serrated.

54. The occipital plate of claim 48, wherein the plate further includes a spinal rod; the spinal rod being positionable in the at least one clamp portion by insertion from a top portion of the assembly.

55. The occipital plate of claim 48, wherein the central portion includes an upper portion, a lower portion, and a grooved portion therebetween, the upper portion having one bone screw hole.

56. The occipital plate of claim 55, wherein the grooved portion is flexible to permit the upper portion to be disposed at an angle with respect to the lower portion.

57. The occipital plate of claim 48, wherein the leg portions and at least a portion of the central portion are disposed in nonparallel planes.

58. The occipital plate of claim 57, wherein the planes intersect at an angle of between about 160° and about 175°.

59. The occipital plate of claim 57, wherein the planes intersect at an angle of about 170°.

60. The occipital plate of claim 48, wherein the bone screw holes, in the lower portion are disposed in a rectangular array.

61. The occipital plate of claim 60, wherein at least one group of bone screw holes in the array is disposed along a central axis of the plate extending between the leg portions.

62. The occipital plate of claim 61, wherein the bone screw hole in the upper portion is disposed on the central axis.

63. The occipital plate of claim 48, wherein at least two bone screw holes are disposed coaxially.

64. The occipital plate of claim 48, wherein the plate further includes a bushing; the at least one bone screw hole being sized and configured to receive the bushing to permit polyaxial angulation.

65. The occipital plate of claim 64, wherein the exterior surface of the bushing has a frustospherical shape.

66. The occipital plate of claim 64, wherein the bushing further includes at least one slot located on a sidewall thereof.

67. The occipital plate of claim 66, wherein the sidewall further includes a ridge.

68. The occipital plate of claim 48, wherein the plate is bendable along at least two generally parallel axes.

69. The occipital plate of claim 48, wherein the plate is bendable along at least two generally perpendicular axes.

* * * * *